(12) United States Patent
Trushkowsky (10) Patent No.: US 6,186,786 B1
(45) Date of Patent: Feb. 13, 2001

(54) DENTAL INSTRUMENT (75) Inventor: Richard Trushkowsky, Morganville, NJ (US)

(73) Assignee: AdDent Inc., Danbury, CT (US)

( * ) Notice: Under 35 U.S.C. 154(b), the term of this patent shall be extended for 0 days.

(21) Appl. No.: 09/453,046

(22) Filed: Dec. 2, 1999

(51) Int. Cl.$^7$ ........................................ A61C 3/08
(52) U.S. Cl. ........................ 433/164; 433/29; 433/141
(58) Field of Search ............................ 433/164, 29, 141, 433/147, 142

(56) References Cited

U.S. PATENT DOCUMENTS

| Re. 13,621 | * | 9/1913 | Kelly | 433/142 |
| 1,356,372 | * | 10/1920 | Kelly | 433/143 |
| 4,617,718 | * | 10/1986 | Andersson | 29/558 |
| 4,666,405 | * | 5/1987 | Ericson | 433/229 |
| 5,178,537 | * | 1/1993 | Currie | 433/72 |
| 5,681,163 | * | 10/1997 | Wolk | 433/3 |

* cited by examiner

Primary Examiner—John J. Wilson
Assistant Examiner—Melba Bumgarner (57) ABSTRACT

A dental instrument for assisting in the filling and curing of a dental restoration with light activated resin composite material(s) having a handle with an elongated body of triangular shape, a first and second end section extending from the elongated body at each opposite end thereof and a first and second opening in each end section in combination with a first and second insert member removably engaging said first and second opening respectively in each of the opposite ends of the handle. Each insert member has a shaped body tapered at one end thereof and indicator means to monitor the depth of the restoration to the pulpal floor and to provide alignment of the preparation relative to the marginal ridge of an adjacent tooth.

16 Claims, 8 Drawing Sheets

DENTAL INSTRUMENT

FIELD OF THE INVENTION

This invention relates to a dental instrument to facilitate the filling of dental cavities with light activated restorative material and more particularly to a dental instrument having a removable and disposable insert member at each opposite end thereof for establishing proximal contact, as well as plugging, shaping and brushing a dental filling. The dental instrument also has indicator means for monitoring the depth of a restorative preparation and for alignment of the preparation with an adjacent tooth.

BACKGROUND OF THE INVENTION

Recent advances in dentin bonding and the increased importance of esthetics in dental restorative preparations have accelerated the use of light activated resin composite materials as filling materials for both anterior and posterior restorations. However, despite improvements in materials and techniques, the placement of the resin composite remains technique sensitive and establishing firm and properly located interproximal contact using resin composite filling materials particularly for posterior restorations remains difficult to achieve. If adequate contact is not achieved after matrix removal, a space will occur with the adjacent tooth. Food impaction may result in decay formation and periodontal disease. The plasticity of resin composite materials prior to the application of light radiation for curing the material makes it difficult to contour the restoration and to establish contact with adjacent teeth. In addition, it is, at present, difficult to cure composite in the deeper recesses of a dental preparation. Moreover, currently available dental instruments do not make accurate contact mesially and distally to provide for adequate approximal contact during hardening and are unable to accommodate different size preparations. Commercially available devices are also unable to gauge or monitor the depth of the restoration or to assist in aligning the preparation with an adjacent tooth. For proper curing of the resin composite light must to able pass from the light curing source into the gingival floor area through the proximal box. Otherwise open margins, sensitivity and recurrent decay will develop. Accordingly, the dental instrument should facilitate the transmission of light into the gingival floor areas.

SUMMARY OF THE INVENTION

The dental instrument of the present invention enables light to pass deep into the proximal box and includes removable and interchangeable insert members at the opposite ends of the instrument handle to readily facilitate the use of the instrument both mesially and distally and is adaptable for use with any size restoration by substituting different size insert members. Moreover, the insert members are disposable. In addition, the instrument handle includes a notch at each opposite end thereof adjacent an opening through which the insert member extends forming a definitive rest stop for the positioning of a conventional light guide against the insert member. The notch also readily aligns the light guide in a substantially concentric relationship with the insert member to assure maximum light transmission through the insert member. Each insert member includes an indicator to monitor the depth of the restoration to the pulpal floor and to assist in alignment of the restorative preparation to the marginal ridge of an adjacent tooth.

The dental instrument of the present invention assists in the filling and curing of a dental restoration with light activated resin composite material(s) and comprises: a handle having an elongated body of triangular shape with a first opening at one end thereof adapted to receive a first removable and disposable insert member and a second opening at the end of the elongated body opposite said first opening with said second opening adapted to receive a second removable and disposable insert member, said first and second insert member being interchangeable with one another for facilitating mesial and distal contact with the filled preparation and having a notch adjacent the location of each opening, said notch having a geometry forming a rest stop for the placement of a light guide against either insert member to establish a substantially concentric relationship therewith when curing the light activated resin composite material in the filling.

The present invention is also directed to a dental instrument having an elongated body of triangular shape forming a handle with a first and second end section extending from the elongated body at each opposite end thereof and a first and second opening in each end section in combination with a first and second insert member removably engaging said first and second opening respectively in each of the opposite ends of the handle with each insert member having a shaped body tapered at one end thereof and indicator means to monitor the depth of the restoration to the pulpal floor and to provide alignment of the preparation relative to the height of the marginal ridge of an adjacent tooth. Each insert member further includes an upper end section of generally cylindrical configuration adapted to be slidably inserted into an opening in one of the opposite ends of the handle and a lower end section having a concave surface on one side thereof and a convex surface on the opposite side with the lower end section tapering downwardly to form a tip which is flat ended and of rectangular geometry.

BRIEF DESCRIPTION OF THE DRAWINGS

Other objects and advantages of the present invention will become apparent from the following detailed description of the present invention when read in conjunction with the accompanying drawings of which.

DETAILED DESCRIPTION OF A PREFERRED EMBODIMENT

Figure 1:
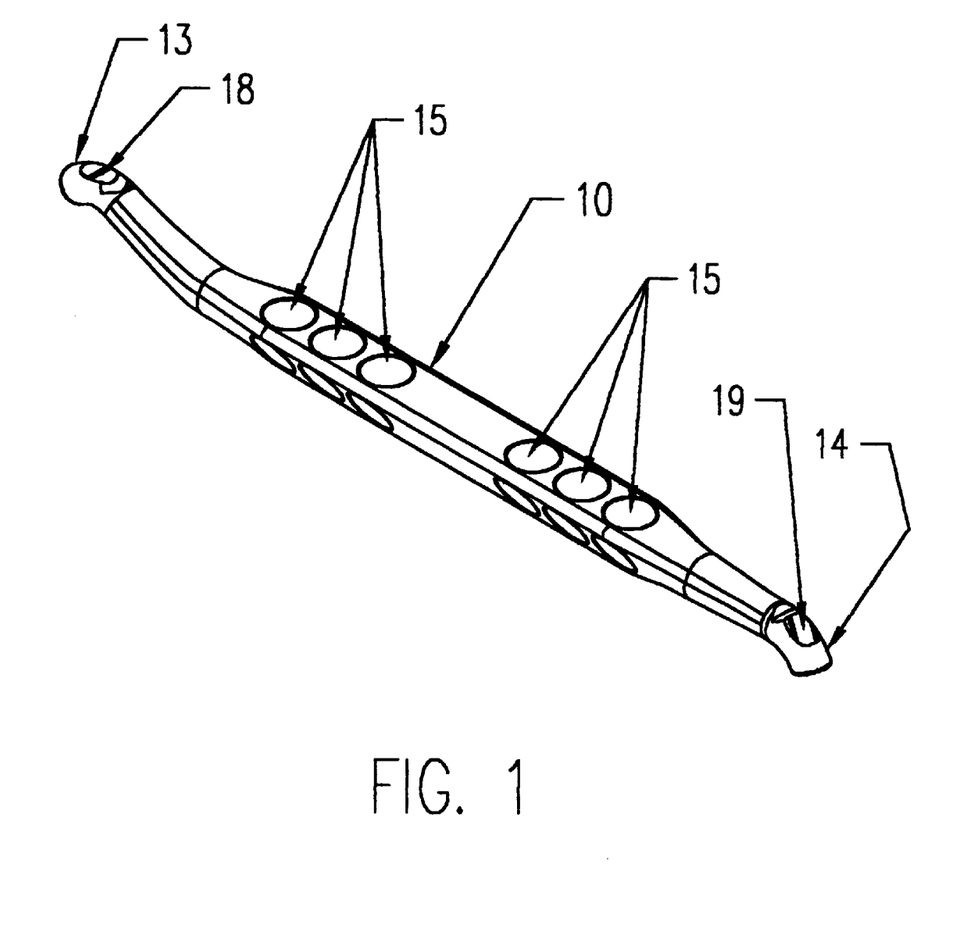
FIG. 1 is perspective view of the handle of the dental instrument of the present invention without the insert members.
Figure 2:
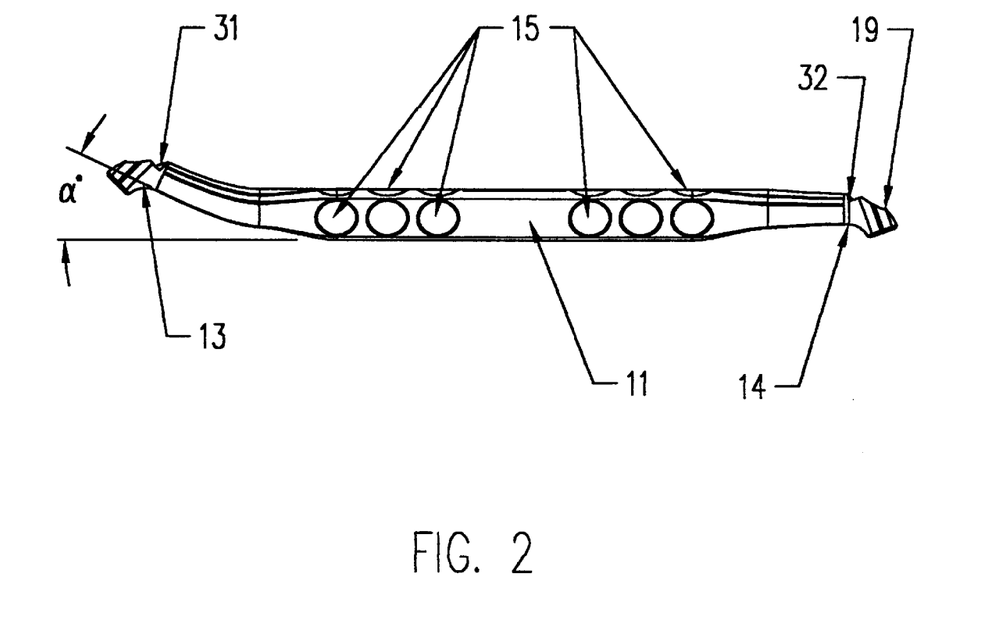
FIG. 2 is a front elevation of the handle of FIG. 1.
Figure 3:
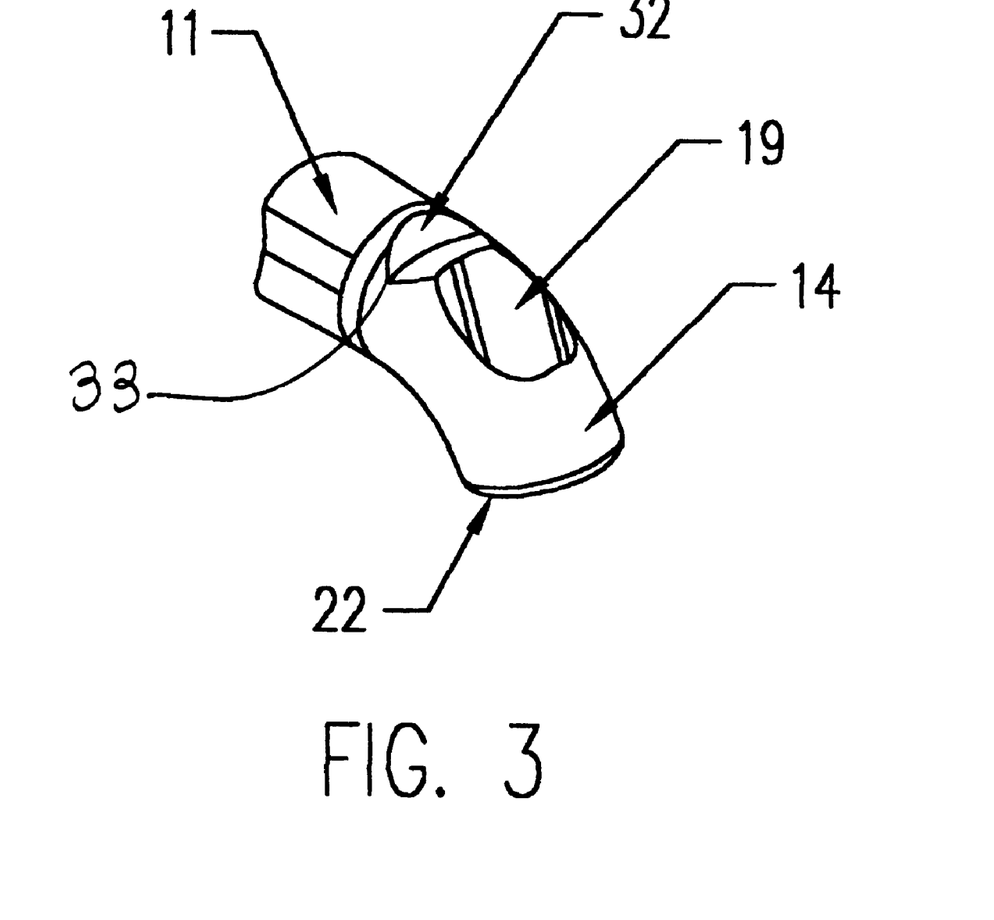
FIG. 3 is an enlargement of one end of the handle of FIG. 1.
Figure 4:
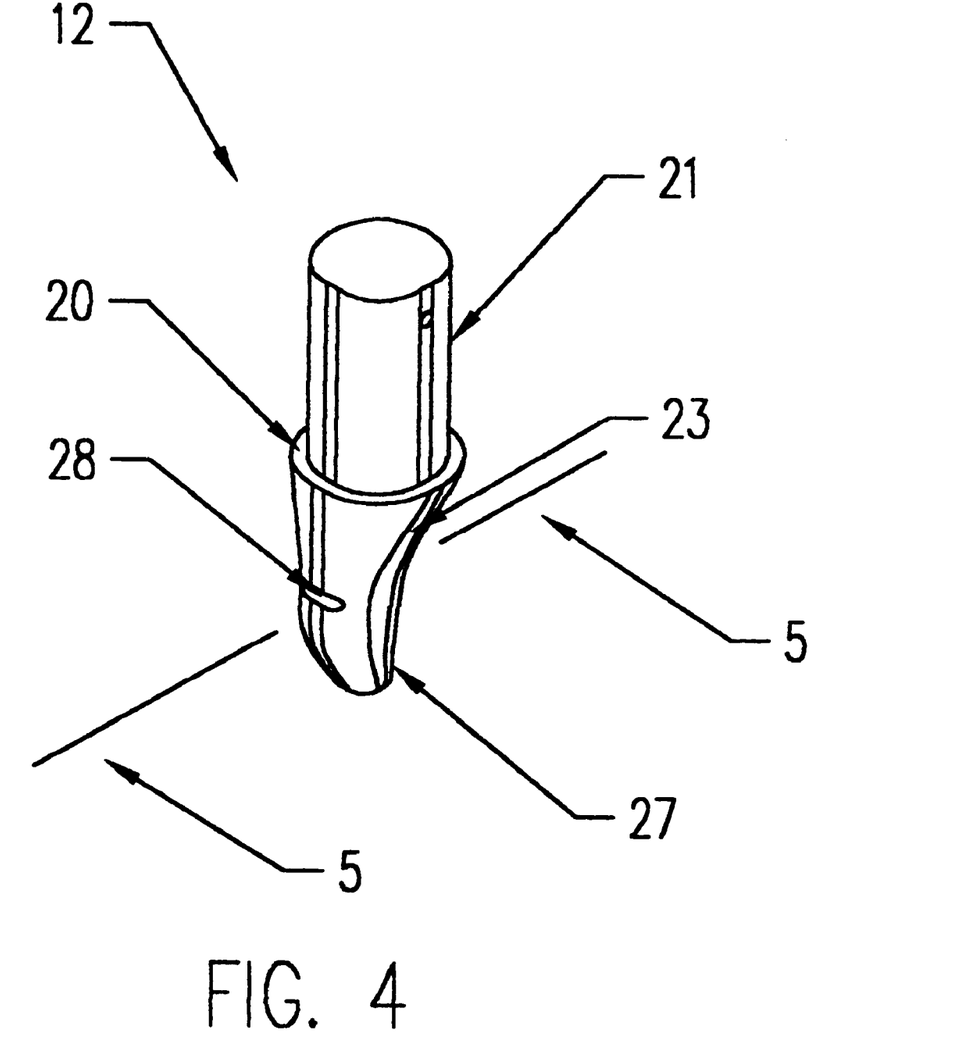
FIG. 4 is an enlarged view in perspective of an insert member adapted to be inserted into an opening at either end of the handle of FIG. 1.
Figures 5, 5A:
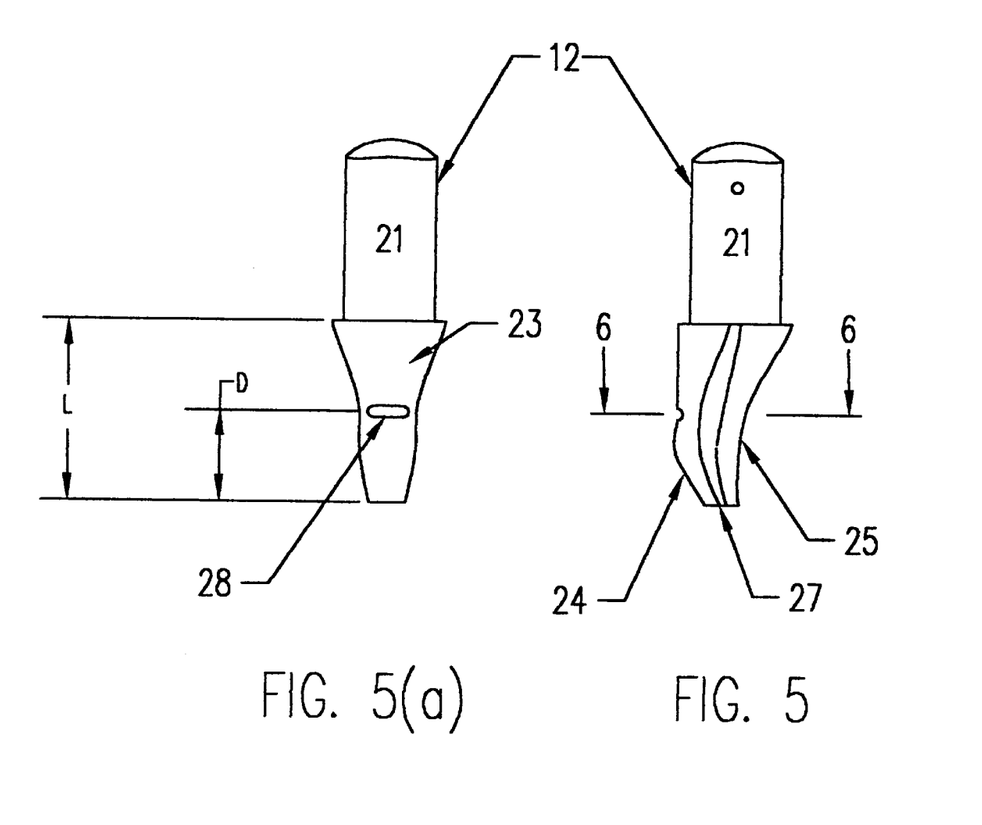
FIG. 5 is a side elevation of the insert member taken along the lines 5—5 of FIG. 4.
FIG. 5(a) is an end view of the insert member of FIG. 5.
Figure 6:
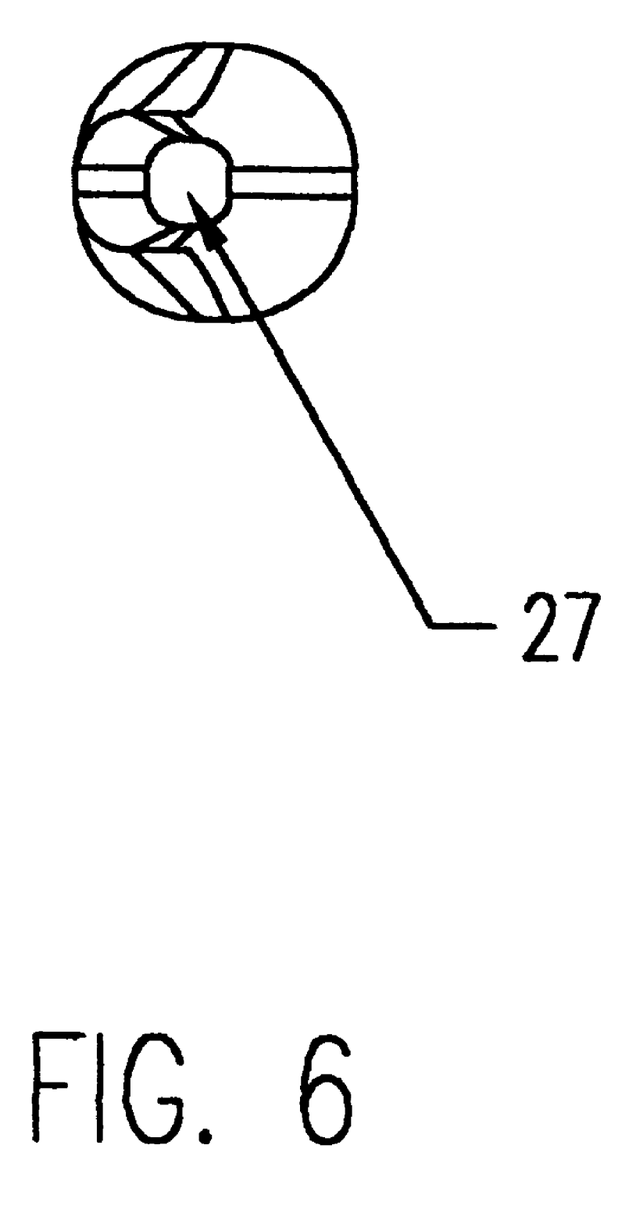
FIG. 6 is a sectional view of the insert member taken along the lines 6—6 of FIG. 5.
Figure 7:
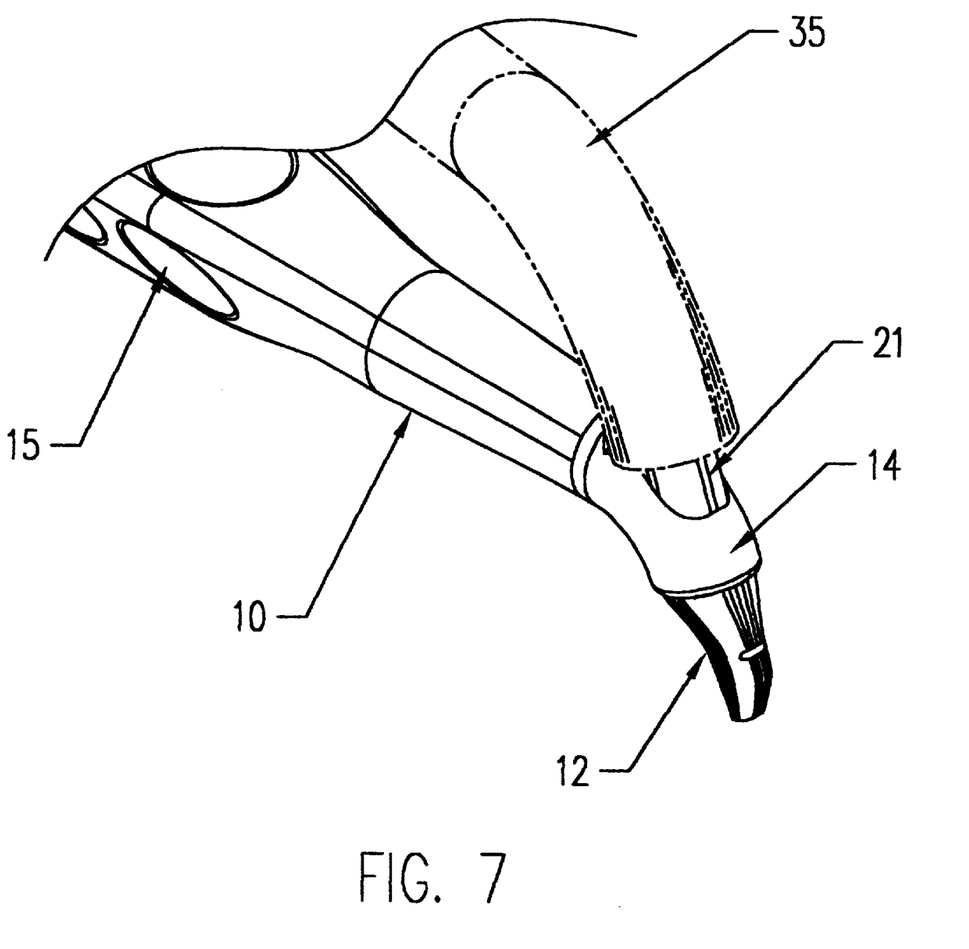
FIG. 7 is a diagrammatic view in perspective of a cutaway section of the handle showing an insert member mounted in the handle at one end thereon and a phantom section of a conventional light guide shown mounted in juxtaposition against the insert member.

The dental instrument of the present invention includes a handle 10 as shown in FIGS. 1–3 for use in combination with an insert member 12 as shown in FIGS. 4–6 and FIGS. 8(a)–8(c) respectively. Each insert member 12 is adapted to be removably mounted in the handle 10 as shown in FIG. 7.

The handle 10 has an elongated body 11 as specifically shown in FIG. 2, preferably of triangular shape, with two end sections 13 and 14 located at each opposite end of the triangular shaped body 11. The triangular shaped body 11 contains a plurality of concave areas 15 which provide recesses along the length of the body 11 to enable the handle 10 to be easily held in one hand in a fixed position and to permit increased torquing efficiency. The handle 10 is bent at the end thereof adjacent the end section 13 to from an inclined angle "α" of between 10 and 25 degrees, preferably 15°, relative to the longitudinal axis of the handle 10. Likewise, although not shown, the handle 10 may be bent adjacent the opposite end section 14 of the handle 10 but to a limited extent of preferably no more than about 5° relative to the longitudinal axis of the handle 10.

Each opposite end section 13 and 14 has an opening 18 and 19 extending therethrough into which the insert member(s) 12 are interchangeably mounted. The openings 18 and 19 are oriented relative to the axial body 11 to permit mounting the insert members 12 in the handle 10 of the dental instrument so that each insert member 12 can establish mesial and/or distal contact with adjacent teeth.

Figure 8:
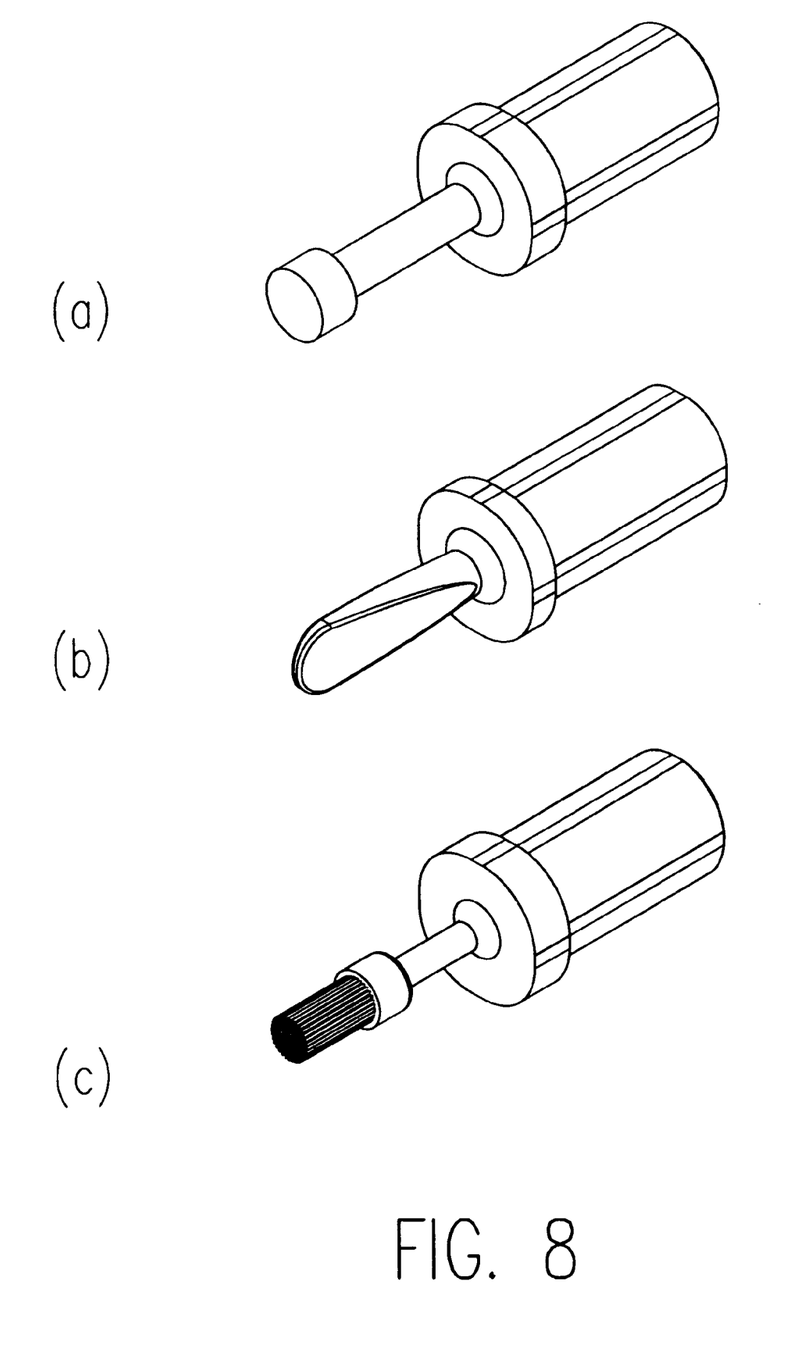
FIG. 8(a) is an enlarged perspective view of an interchangeable dental insert member specifically designed in accordance with the present invention to perform the function of plugging.
FIG. 8(b) is an enlarged perspective view of an interchangeable dental insert member specifically designed in accordance with the present invention to perform the function of shaping.
FIG. 8(c) is an enlarged perspective view of an interchangeable dental insert member specifically designed in accordance with the present invention to perform the function of brushing.

Each insert member 12 is preferably of a transparent plastic composition having a predetermined optical transmissivity. However, inserts may be composed of materials of different optical transmissivities to control the speed and degree of polymerization of the dental filling material in the restoration. Since it is known in the literature that high initial curing energy can cause material shrinkage, the transmissivity characteristic of the insert can thus be used to control material shrinkage and strain in the restoration. The insert members 12, as more clearly shown in FIG. 4, have an upper end section 21 so that they may be interchangeably mounted in the openings 18 and 19 of the handle 10. Moreover, the upper end section 21 of each insert member 12 is sized and shaped commensurate with the size and shape of the openings 18 and 19 to establish a friction fit in each of the openings 18 and 19 when slidably inserted but which permits each insert 12 to be removed therefrom. The insert members 12 also have a lower end section 23 which may be identical in shape to one another. However, the insert members 12 may be of different length and width so as to fit into an existing preparation and may have different shapes to provide different functions such as plugging, shaping and brushing as shown in FIGS. 8(a)–8(c) respectively and to accommodate pre-molar, molar and deciduous teeth.

The upper end section 21 of each insert member 12 and the geometry of the openings 18 and 19 is preferably cylindrical although other geometries such as a square geometry may be used. A cylindrical geometry permits the insert member 12 to be rotated in the opening 18 or 19 to accommodate mesial or distal contact. The diameter of the cylindrical upper section 21 should be slightly smaller than the diameter of the lower section 23 at the junction adjoining the two sections 21 and 23 respectively so as to form a ledge 20 which will abut the distal end of each of the end sections 13 and 14 upon mounting the insert member 12 into the handle 10. The lower end section 23 of each insert member 12 is shaped to form a convex surface 24 on one side thereof and a concave surface 25 on the opposite side thereof as shown in FIG. 5. The lower end section 23 of each insert member 12 also tapers downwardly from the ledge 20 with the convex and concave surfaces 24 and 25 gradually decreasing in diameter to converge into a flat ended tip 27 of substantially rectangular configuration at the distal end thereof as shown in FIG. 6. The flat ended tip 27 is sized to provide access into a prepared tooth for condensing the filling material and permits light curing at the gingival terminus. The lower end section 23 of each insert member 12 has a marking 28, preferably represented by a groove, which is substantially horizontal and parallel to the flat ended tip 27 at a predetermined height "D" relative to the length "L" of the lower end section 23 of insert 12. The marking or groove 28 functions as a visual indicator for monitoring the depth of the restoration to the pulpal floor and to assist in the alignment of the restoration both in height and position with the marginal ridge of an adjacent tooth. Height "D" will vary between 2 mm and 6 mm depending on the depth of the preparation. Accordingly, the marking 28 can be represented by any form of visual indicator including a printed marking. The greatest height of curvature is approximately 1 mm below the groove. The outer periphery of the lower end section 23 may be textured to provide the function of a mechanical lock for subsequently placed composite material.

A notch 31 and 32 is formed in the end sections 13 and 14 of the handle 10 adjacent the openings 18 and 19. Each of the notches 31 and 32 has a "V" shaped configuration in cross section forming an apex 33. The notches 31 and 32 function as a rest stop for the placement of a conventional optical light guide 35 as shown in phantom in FIG. 7 against the upper section 21 of either one of the insert member(s) 12. The light guide 35 is held on place in the notch 31 or 32 of an insert member 12 to maintain the light guide 35 in substantial coaxial relationship with the upper end section 21 of the insert member 12 when curing the filling.

What is claimed is:

1. A dental instrument for assisting in the filling and curing of a dental restoration with light activated restorative material(s) comprising: a handle having an elongated body of triangular shape with a first opening at one end thereof adapted to receive a first removable and disposable insert member and a second opening at the end of the elongated body opposite said first opening with said second opening adapted to receive a second removable and disposable insert member, said first and second insert member being interchangeable with one another for facilitating mesial and distal contact with an adjacent tooth and having a notch adjacent the location of each opening, said notch having a geometry forming a rest stop for the placement of a light guide against either insert member to establish a substantially concentric relationship therewith when curing the light activated restorative material in the filling.

2. A dental instrument as defined in claim 1 wherein said handle has a first and second end section extending from the opposite ends of said body with said first opening formed in said first end section and said second opening formed in the second end section and with said first end section lying at an inclined angle "α" of between 10 and 25 degrees relative to the longitudinal axis of said body.

3. A dental instrument as defined in claim 2 wherein said second end section lies in a range of from substantially level to 5 degrees with the longitudinal axis of said body.

4. A dental instrument as defined in claim 3 wherein the handle further includes a plurality of depressions along said body which facilitates the placement of the users finger(s) in holding the instrument.

5. A dental instrument as defined in claim 4 wherein said first and second opening has a geometry selected from the group consisting of square and cylindrical.

6. A dental instrument as defined in claim 1 wherein each insert member includes indicator means to monitor the depth of the restoration to the pulpal floor and to provide alignment of the preparation relative to the marginal ridge of an adjacent tooth.

7. A dental instrument as defined in claim 6 wherein said indicator means comprises a horizontal groove lying substantially parallel to the flat ended tip.

8. A dental instrument for assisting in the filling and curing of a dental restoration with light activated restorative material(s) comprising: a handle having an elongated body of triangular shape, a first and second end section extending from the elongated body at each opposite end thereof and a first and second opening in each end section in combination with a first and second insert member removably engaging said first and second opening respectively in each of the opposite ends of the handle with each insert member having a shaped body tapered at one end thereof and indicator means to monitor the depth of the restoration to the pulpal floor and to provide alignment of the preparation relative to the marginal ridge of an adjacent tooth.

9. A dental instrument as defined in claim 8 wherein said first end section lies at an inclined angle "α" of between 10 and 25 degrees relative to the longitudinal axis of said body.

10. A dental instrument as defined in claim 9 wherein said second end section lies in a range of from substantially level to 5 degrees with the longitudinal axis of said body.

11. A dental instrument as defined in claim 10 wherein said first and second opening has a geometry selected from the group consisting of square and cylindrical.

12. A dental instrument as defined in claim 11 wherein the handle of the dental instrument further includes a plurality of depressions along said body which facilitates the placement of the users finger(s) in holding the instrument.

13. A dental instrument as defined in claim 8 wherein each insert member includes an upper end section of generally cylindrical configuration adapted to slidably engage into said first and second opening and a lower end section having a concave surface on one side thereof and a convex surface on an opposite side thereof.

14. A dental instrument as defined in claim 13 wherein the diameter of the upper cylindrical section is smaller than the diameter of the lower end section at the junction therebetween so as to form a ledge which provides a stop when an insert member is placed into the first or second opening.

15. A dental instrument as defined in claim 14 wherein said lower end section tapers downwardly from said adjoining junction with the convex and concave surfaces converging into a flat ended tip having a substantially rectangular configuration.

16. A dental instrument as defined in claim 14 wherein each insert has a different optical transmissivity.

\* \* \* \* \*